United States Patent
Hansen et al.

(10) Patent No.: US 8,734,434 B2
(45) Date of Patent: May 27, 2014

(54) SKIN COOLING FOR A DERMATOLOGIC TREATMENT PROCEDURE

(75) Inventors: Lars Kurt Hansen, Taastrup (DK); Keld Schmidt, Bagsværd (DK)

(73) Assignee: Ellipse A/S (DK)

( * ) Notice: Subject to any disclaimer, the term of this patent is extended or adjusted under 35 U.S.C. 154(b) by 1490 days.

(21) Appl. No.: 12/193,845

(22) Filed: Aug. 19, 2008

(65) Prior Publication Data

US 2009/0054882 A1    Feb. 26, 2009

(30) Foreign Application Priority Data

Aug. 24, 2007    (EP) .................................... 07114956

(51) Int. Cl.
*A61B 18/18*    (2006.01)

(52) U.S. Cl.
USPC ........... 606/9; 606/2; 606/15; 606/16; 606/20

(58) Field of Classification Search
None
See application file for complete search history.

(56) References Cited

U.S. PATENT DOCUMENTS

| | | | |
|---|---|---|---|
| 3,307,553 A | 3/1967 | Liebner | |
| 7,041,094 B2 * | 5/2006 | Connors et al. | 606/9 |
| 2001/0009997 A1 * | 7/2001 | Pope et al. | 606/9 |

FOREIGN PATENT DOCUMENTS

| | | |
|---|---|---|
| GB | 2 390 025 A | 12/2003 |
| JP | 2003-000334 | 1/2003 |
| WO | WO 99/05978 | 2/1999 |
| WO | WO 99/27863 | 6/1999 |
| WO | WO 00/23018 | 4/2000 |
| WO | WO 2006/089227 A2 | 8/2006 |

* cited by examiner

*Primary Examiner* — Bill Thomson
*Assistant Examiner* — Joseph D Harris
(74) *Attorney, Agent, or Firm* — Ostrolenk Faber LLP

(57) ABSTRACT

A skin cooling method for a dermatologic treatment procedure, by which a skin target region is exposed for a specified duration to irradiation with electromagnetic energy emitted from an electromagnetic energy exit opening of a skin treatment applicator and the target region is cooled at least during part of the duration of the exposure to electromagnetic energy irradiation, wherein a cooling procedure is performed including an air cooling step comprising ejection of a directional flow of cooling air towards the skin treatment region, said directional cooling air flow having a temperature T in the interval $0°\,C. < T \leq 15°\,C$. In an apparatus according to the invention this method may be combined with one or more contact cooling steps.

18 Claims, 4 Drawing Sheets

US 8,734,434 B2

SKIN COOLING FOR A DERMATOLOGIC TREATMENT PROCEDURE

INTRODUCTION

Figure 1:
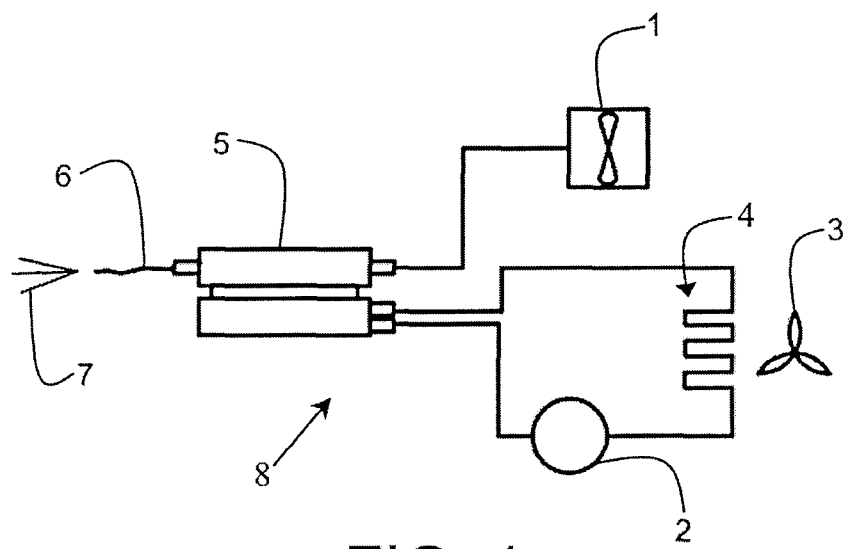

The present invention relates to a skin cooling method, a skin cooling apparatus for a dermatologic treatment procedure by which a skin target region is exposed for a specified duration to irradiation with electromagnetic energy emitted from an electromagnetic energy exit opening of a skin treatment applicator and the target region is cooled at least during part of the duration of the exposure to electromagnetic energy irradiation. The invention further relates to a method for obtaining a treated skin region.

BACKGROUND ART

In the field of skin cooling for dermatologic treatment procedures it is generally known to provide skin cooling during treatment by the use of cryogen cooling air.

From JP 203000334 A2 it is for instance known to provide air cooling by the use of a cooling arrangement in which the cooling air is provided from the cold side of a Peltier-element, where the warm side of said Peltier-element is water cooled. The cooled air having a temperature in the range of −15--10° C. is blown out through a handheld applicator, which is connected with the Peltier-element through an air hose.

It is also known from WO 99/05978 to use supercooled tetrafluoroethane having a temperature of −26° C. to cool an area of treatment during a surgical procedure.

Furthermore it is known from WO 00/23018 to use a supercooled airflow to cool a skin-contacting surface.

These prior art skin cooling methods have several drawbacks. First of all the use of sub-zero cooling air temperatures to achieve sufficient skin cooling generally provide an inconvenient risk of inflicting chill damage to the skin undergoing treatment. Also there is risk of a formation of ice crystals in the flow of cooling air, potentially inflicting damage on the treatment apparatus and skin undergoing treatment.

Moreover when a transparent skin-contacting surface is placed in the beam path for cooling the skin undergoing treatment this imposes a loss of electromagnetic energy as the emitted electromagnetic energy must pass through the skin-contacting surface on its way to the treatment region. Therefore, the prior art methods are relatively energy consuming, and the applicators used in connection with the known methods are rather complicated and impractical in use.

Hence it is the object of the invention to provide a skin cooling method and a skin cooling apparatus by which the abovementioned drawbacks are eliminated or reduced significantly and that will simplify dermatologic treatment procedures considerably.

SUMMARY OF THE INVENTION

In a first aspect of the invention this object is achieved by a skin cooling method for a dermatologic treatment procedure comprising the steps of:

a) exposing a skin target region for a specified duration to irradiation with electromagnetic energy emitted from an electromagnetic energy exit opening of a skin treatment applicator and b) cooling the skin target region at least during part of the duration of the exposure to the electromagnetic energy irradiation, wherein the cooling procedure includes an air cooling step comprising ejection of a directional flow of cooling air towards the skin treatment region, said directional cooling air flow having a temperature T in the interval $0°$ C.$<T\leq15°$ C.

It has been shown that a skin cooling method using cooling air of a temperature in the abovementioned range provides for a simple way of performing dermatologic skin treatment with sufficient cooling of the skin while at the same time eliminating the hitherto existing risk of chill damage to the skin under treatment as well as the risk of ice crystal formation in the flow of cooling air as cryogen cooling is no longer used.

In a preferred development of the method according to the invention the cooling air flow is supplied with a flow rate of between about 10 and about 20 l/min, which has been shown to provide sufficient cooling of the skin during the treatment procedure with significantly improved energy efficiency.

In a further preferred development of the method according to the invention the air cooling step is performed during the exposure of the skin target region to irradiation with electromagnetic energy, thereby providing a method in which skin is exposed directly to electromagnetic energy thus ensuring that no electromagnetic energy will be lost during skin exposure.

In a particularly preferred development of the method according to the invention the cooling procedure further comprises at least one contact cooling step provided by a cooled skin contacting surface area of a part of a housing for the skin treatment applicator.

Addition of one or more contact cooling steps to the air cooling step provides for a skin cooling method providing additional cooling of the skin before, during and/or after treatment in a particularly simple and practical way. Furthermore the method may be performed without loss of electromagnetic energy and therefore with higher efficiency, as contact cooling may be performed solely by the area of the housing adjacent to the electromagnetic energy exit opening.

In a further preferred development of the method according to the invention the cooled skin contacting surface is cooled by the directional flow of cooling air ejected during said air cooling step, whereby the method may be performed using the same source of cooling air for the air cooling step and the contact cooling step.

In a second aspect of the invention the object is achieved by providing a skin cooling apparatus for a dermatologic treatment procedure, comprising a skin treatment applicator having an electromagnetic energy exit opening for emission of electromagnetic energy for irradiation of a skin treatment region and means for cooling of the skin target area during at least a part of the duration of exposure of the skin target region to the electromagnetic energy irradiation, wherein said cooling means of the skin cooling apparatus comprises an air flow ejection means adjacent to the electromagnetic energy exit opening, a single cooling source being provided for supplying a cooling air flow to the air flow ejection means for ejection of a directional cooling air flow therefrom, said cooling source being capable of providing a cooling air flow having a temperature T in the interval $0°$ C.$<T\leq15°$ C.

Such an apparatus provides a simple way of carrying out a skin cooling method according to the invention, thus providing the advantage of sufficient cooling of the skin while at the same time eliminating the risk of chill damage and the risk of ice crystal formation in the chilled air flow.

In a further embodiment of the apparatus according to the invention the cooling means of the skin treatment applicator further comprises a skin contacting surface area of a part of a housing for the skin treatment applicator and air flow distribution means for supplying said cooling air flow from the single cooling source to the skin contacting surface area and the air flow ejection means. Thereby is provided a particularly simple apparatus for dermatologic treatment, which may carry out a method according to the invention, thus providing sufficient cooling of the skin before, during and after exposure by combining contact cooling and air cooling.

In a further embodiment of the apparatus according to the invention the skin contacting surface area is disposed adjacent to said electromagnetic energy exit opening to be cooled by the directional cooling air flow from said air flow ejection means, whereby is provided an apparatus which may use the same source of cooling air for the air cooling step and the contact cooling step.

In a further embodiment of the apparatus according to the invention the single cooling source comprises an electrically operated heat exchanger including a cold side and a warm side arranged in heat energy transfer relationship with a distribution system for said cooling air flow and a circulation system for a secondary cooling medium, respectively, the distribution and circulation systems being connected with a high-pressure air generator and a secondary cooling system, respectively, disposed externally with respect to the skin treatment applicator. Thereby an apparatus is provided which is considerably easier to use and which provides for safe and energy efficient cooling of the skin before, during and after exposure.

In further embodiments of the apparatus according to the invention the electrically operated heat exchanger comprises a Peltier-element, the air flow ejection means comprises an air duct in flow communication with said distribution system and terminating in a nozzle-like air outlet in a perimeter wall of the electromagnetic energy exit opening of the skin treatment applicator and the electrically operated heat exchanger is disposed inside the skin treatment applicator.

Hereby a further simplified apparatus is provided, which may be used for performing all sorts and types of dermatologic treatments in a simple and reliable way.

In a further preferred embodiment of the apparatus according to the invention the high-pressure air generator is controlled to supply an air flow to the first circulation system producing at the air flow ejection means a flow rate between 10 and 20 l/min., whereby a simple apparatus with improved energy efficiency is provided.

According to a third aspect of the invention a method for obtaining a skin region treated with electromagnetic energy is aimed at. The method comprises the steps of a) exposing a skin target region for a specified duration to irradiation with electromagnetic energy emitted from an electromagnetic energy exit opening of a skin treatment applicator and b) cooling the skin target region at least during part of the duration of the exposure to the electromagnetic energy irradiation, wherein the cooling procedure includes an air cooling step comprising ejection of a directional flow of cooling air towards the skin treatment region, said directional cooling air flow having a temperature T in the interval $0°\,C. < T \leq 15°\,C.$

SHORT DESCRIPTION OF THE DRAWINGS

Figure 3:
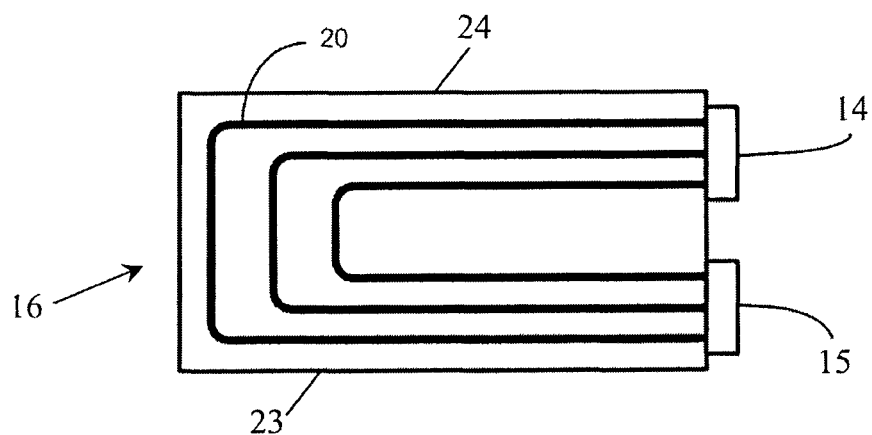
Figure 4:
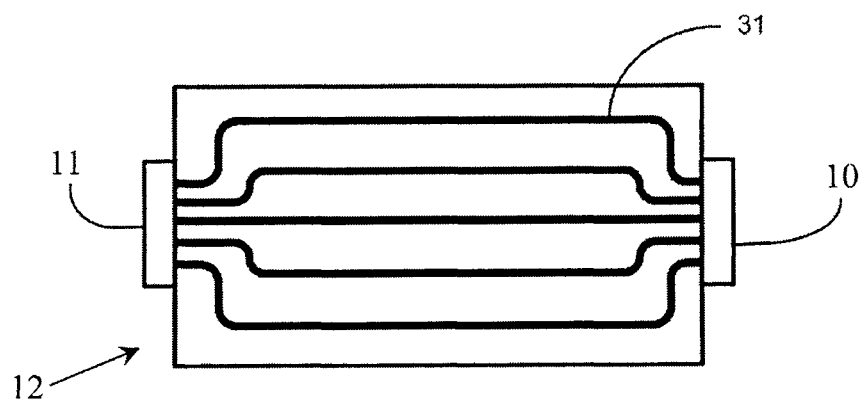
Figure 5:
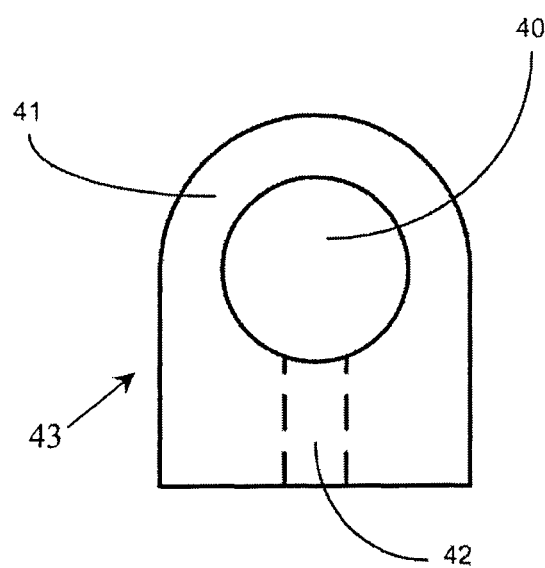
Figure 6:
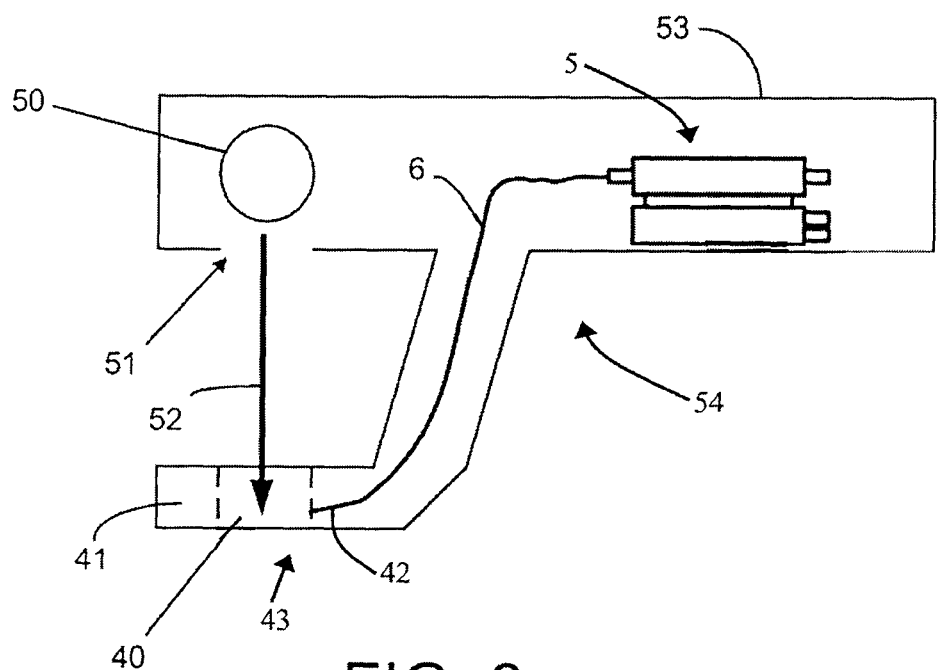

The invention will now be described in further detail based on a non-limiting exemplary embodiment, and with reference to the drawings. In the drawings, FIG. 1 shows a schematic overview of a skin cooling apparatus according to the invention, FIG. 2 shows a schematic side view of a heat exchanger component of a skin cooling apparatus according to the invention, FIG. 3 shows schematically a cross-sectional side view of a water-cooled component of the heat exchanger component of a skin cooling apparatus according to the invention, FIG. 4 shows schematically a cross-sectional top view according to the line IV-IV of FIG. 2 of an air cooling component of the heat exchanger component of a skin cooling apparatus according to the invention, FIG. 5 shows a skin contacting member of a skin treatment applicator according to the invention, and FIG. 6 shows an embodiment of a skin treatment applicator according to the invention.

DETAILED DESCRIPTION OF THE INVENTION

With reference to FIG. 1 an embodiment of a skin cooling apparatus 8 according to the invention is shown. Such an apparatus 8 comprises in the embodiment shown a compressor 1 providing compressed air, a heat exchanger 5 for cooling the compressed air, a pump 2 for circulating cooling water used for cooling the heat exchanger 5, a radiator 4 for lowering the temperature of the cooling water circulated by the pump 2 and a fan 3 for cooling the radiator 4. The air provided by the compressor 1 is lead through the heat exchanger 5 in which it is cooled down to achieve a temperature T in the range $0°\,C. < T \leq 15°\,C.$ The cooled air 7 is supplied form the heat exchanger 5 through an air output member 6, e.g. a pipe or hose or the like, for leading cooled air towards air flow ejection means as will be discussed further in the following.

Figure 2:
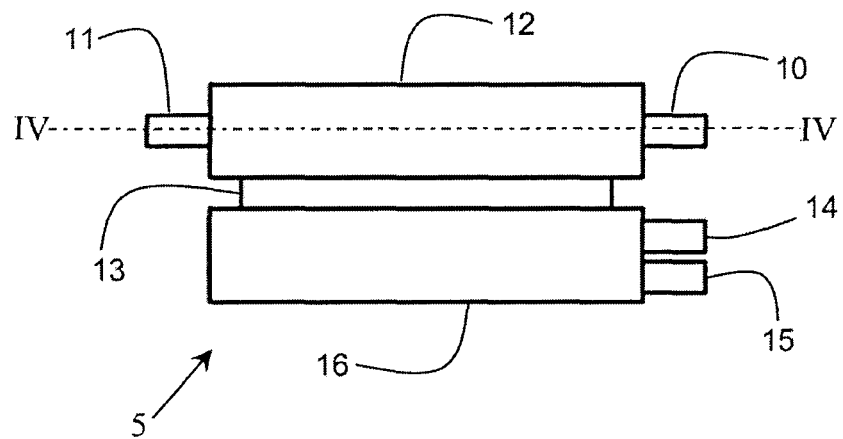

FIG. 2 shows a more detailed view of an embodiment of a heat exchanger 5. The heat exchanger 5 comprises an air cooling component 12 comprising an air input 10 for non-cooled air provided by the compressor 1 shown in FIG. 1 and an air output 11 for cooled air placed in an opposite end of the air cooling component 12. The air cooling component 12 is arranged in contact with the cool side of a Peltier-element 13 thus providing for cooling of the air flow through the air cooling component 12 from the air input 10 to the air output 11. The warm side of the Peltier-element 13 is in contact with a water-cooled component 16 for removing heat from the Peltier-element. The water-cooled component 16 comprises a cooling water input 14 and a cooling water output 15 for connection to the pump 2 and radiator 4 shown in FIG. 1.

For further details FIG. 3 shows a schematic view of the water-cooled component 16 in FIG. 2. The water-cooled component 16 comprises an upper surface 24 and a lower surface 23, the upper surface 24 being in contact with the Peltier-element 13 as shown in FIG. 2. The water-cooled component 16 further comprises the cooling water input 14 and the cooling water output 15 between which cooling water flows from the input 14 through a number of water conduits 20 arranged to take up heat from the Peltier-element abutting upper surface 24 to the output 15.

Correspondingly, FIG. 4 shows a schematic sectional view of the air cooling component 12 as seen along the section line IV-IV of FIG. 2. The air cooling component 12 comprises as shown an air input 10 and an air output 11, between which a number of air conduits 31 lead air provided by the compressor 1 shown in FIG. 1 from the air input 10 to the air output 11. A hose, pipe or the like such as the air output member 6 shown in FIG. 1 may be connected to the air output 11 for the purpose of leading the cooled air towards air flow ejection means. The air flow is supplied through the air output member 6 with a low energy content, since it preferably comprises a temperature T in the range $0°\,C. < T \leq 15°\,C.$ and/or a flow rate in the range of 10 to 20 l/min.

FIG. 5 shows schematically a preferred embodiment of a skin contacting member 43 of a skin treatment applicator adapted to perform both air cooling and contact cooling. The skin contacting member 43 comprises a bore 40 having a diameter in the order of 10 mm, a rim 41 surrounding the bore 40 and an air duct 42 to lead cooled air to the bore 40. The air duct 42 terminates at one end in an air outlet in a perimeter wall of the bore 40, and is connected at its opposite end to the air output member 6. In alternative embodiments the skin contacting member may however be adapted for air cooling only, for instance by having an un-cooled rim.

During treatment of a patient's skin using a skin contacting member 43 as shown in FIG. 5 electromagnetic energy from an electromagnetic energy source (not shown), generally being a light (ultra-violet, visible or infrared) source or microwave source, is emitted through the bore 40 to expose the skin to the radiation. Cooled air for cooling the exposed skin, preferably during exposure, is in the embodiment shown supplied from the skin cooling apparatus 8 via a hose or the like such as the air output member 6 into the duct 42 through the bore 40 and ejected towards the skin as a directional air flow. On the way through the bore 40 the cooled air provides cooling of the rim 41 of the skin contacting member 43, the rim 41 thereby providing the contact cooling according to the invention. To this end the rim 41 comprises a material suited for the purpose, in other words a material having good heat conducting properties such as e.g. aluminium or copper.

Thereby the same cooling source may be used both for direct air cooling and for enabling contact cooling, thus simplifying the skin contacting member 43 by only necessitating one supply line for a cooling air flow. In the embodiment shown the only other thing to be connected to the skin contacting member 43 is the light source. As such the skin contacting member 43 may be galvanic separated from any live elements of the system, which poses the additional advantage of reducing the risk of the patient getting electrically shocked during treatment to an absolute minimum.

For easy and practical use during skin treatment of a patient the skin contacting member 43 is placed in a skin treatment applicator, which is generally a handheld unit. FIG. 6 shows an embodiment of a skin treatment applicator 54 comprising a skin contacting member 43, a heat exchanger 5, an air output member 6 and an electromagnetic energy source 50. These components are encased in an applicator casing 53, which is adapted to be handheld and which comprises an aperture 51 through which an emission of radiation from the electromagnetic energy source 50 as illustrated by the arrow 52 may be directed through the bore 40 and towards a skin target region with which the skin contacting member 43 is placed in contact. According to the invention, the heat exchanger 5 may be made as small as about 60 mm in length. This size of the heat exchanger 5 is sufficiently small to warrant that it may be placed in the handheld device in galvanic separation from the skin contacting member 43, and at the same time with a relatively short transfer distance for the cooled air to minimize energy loss. Also the electric components of the electromagnetic energy source 50 are galvanic separated from the skin contacting member 43, which is as shown only connected with the air output member 6. Hence this embodiment ensures that all current-carrying components are galvanic separated form the skin contacting member 43.

In another embodiment the heat exchanger 5 may be placed remote from the skin treatment applicator, and only connected thereto by the air output member 6. That is, of the cooling system elements the skin treatment applicator may in this alternative embodiment comprise the skin contacting member 43 and the air output member 6 connected thereto only.

It should be noted that the above description of preferred embodiments is merely an example, and that the skilled person would know that numerous variations are possible without departing from the scope of the claims.

The invention claimed is:

1. A skin cooling method performed as part of a dermatologic treatment procedure using a skin cooling apparatus comprising a skin treatment applicator including an electromagnetic energy exit opening for emission of electromagnetic energy, an air flow ejector adjacent to the electromagnetic energy exit opening including a perimeter wall, the air flow ejector comprising an air duct in flow communication with a distribution system for distributing cooling air, the air flow ejector terminating in a nozzle-like air outlet in the perimeter wall of the light exit opening of the skin treatment applicator, the air duct extending inclined with respect to a direction perpendicular to the light exit opening in the direction of an emission of electromagnetic energy, the method comprising:

cooling the skin target region at least during part of an exposure to electromagnetic energy irradiation, the exposure performed for a specified duration by irradiation with electromagnetic energy emitted from an electromagnetic energy exit opening of a skin treatment applicator, wherein the cooling includes an air cooling step comprising ejection of a directional flow of cooling air towards the skin treatment region, said directional cooling air flow having a temperature T in the interval $0° C. < T \leq 15° C.$ 2. The skin cooling method according to claim 1, wherein the flow is supplied with a temperature between 3 and 15° C.

3. The skin cooling method according to claim 1, wherein the directional cooling air flow is supplied with a flow rate of between 10 and about 20 l/min.

4. The skin cooling method according to claim 1, wherein the air cooling step is performed during an entire operation of the exposure of the skin target region to irradiation with electromagnetic energy.

5. The skin cooling method according to claim 1 wherein the cooling further comprises at least one contact cooling step provided by a cooled skin contacting surface area of a part of a housing for the skin treatment applicator.

6. The skin cooling method according to claim 5, wherein the cooled skin contacting surface area is cooled by the directional flow of cooling air ejected during said air cooling step.

7. A skin cooling apparatus for a dermatologic treatment procedure, the skin cooling apparatus comprising:

a skin treatment applicator including an electromagnetic energy exit opening for emission of electromagnetic energy, the electromagnetic energy exit opening positioned and configured to irradiate by the electromagnetic energy a skin treatment region; and a skin cooling unit configured to cool the skin target area during at least a part of the duration of exposure of the skin target region to the electromagnetic energy irradiation, wherein said skin cooling unit of the skin cooling apparatus comprises:

an air flow ejector adjacent to the electromagnetic energy exit opening; and a single cooling source configured to supply cooling air flow to the air flow ejector for ejection of a directional cooling air flow therefrom, said cooling source configured to provide a cooling air flow having a temperature T in the interval $0° C. < T \leq 15° C.$;

the skin cooling apparatus further comprising:

a distribution system positioned and configured to distribute the cooling air flow; and a circulation system positioned and configured for a secondary cooling medium, wherein the single cooling source comprises an electrically operated heat exchanger including:

a cold side and a warm side arranged in heat energy transfer relationship with the distribution system and the circulation system, respectively;

a high-pressure air generator and a secondary cooling system positioned externally with respect to the skin treatment applicator, the distribution system and the circulation system being connected with the high-pressure air generator and the secondary cooling system, wherein the light exit opening of the skin treatment applicator comprises a perimeter wall, wherein the air flow ejector comprises:

a nozzle-like air outlet; and an air duct in flow communication with said distribution system and terminating in the nozzle-like air outlet in the perimeter wall of the light exit opening of the skin treatment applicator, the air duct extending inclined with respect to a direction perpendicular to the light exit opening in the direction of emission of electromagnetic energy.

8. The skin cooling apparatus according to claim 7, wherein said single cooling source is configured to deliver air flow with a temperature between 3 and 15° C.

9. The skin cooling apparatus according to claim 7, wherein the skin treatment applicator comprises a housing, and wherein said skin cooling unit of the skin treatment applicator further comprises:

a skin contacting surface area of a part of a housing for the skin treatment applicator; and air flow distributor configured to supply said cooling air flow from the single cooling source to the skin contacting surface area and the air flow ejector.

10. The skin cooling apparatus according to claim 9, wherein the skin contacting surface area is disposed adjacent to said electromagnetic energy exit opening and is positioned and configured to be cooled by the directional cooling air flow from said air flow ejector.

11. The skin cooling apparatus according to claim 7, further comprising:

a distribution system positioned and configured to distribute the cooling air flow; and a circulation system positioned and configured a secondary cooling medium, wherein the single cooling source comprises an electrically operated heat exchanger including:

a cold side and a warm side arranged in heat energy transfer relationship with the distribution system and the circulation system, respectively, the distribution and circulation systems being connected with a high-pressure air generator and a secondary cooling system, respectively, disposed externally with respect to the skin treatment applicator.

12. The skin cooling apparatus according to claim 11, wherein the electrically operated heat exchanger comprises a Peltier-element.

13. The skin cooling apparatus according to claim 11, wherein the light exit opening of the skin treatment applicator comprises a perimeter wall, and wherein the air flow ejector comprises:

a nozzle-like air outlet; and an air duct in flow communication with said distribution system and terminating in the nozzle-like air outlet in the perimeter wall of the light exit opening of the skin treatment applicator.

14. The skin cooling apparatus according to claim 11, wherein the electrically operated heat exchanger is disposed inside the skin treatment applicator.

15. The skin cooling apparatus according to claim 11, wherein said high-pressure air generator is configured to be controlled to supply an air flow to said distribution system producing at said air flow ejector a flow rate between 10 and 20 l/min.

16. A method for obtaining a skin region treated with electromagnetic energy using a skin cooling apparatus comprising a skin treatment applicator including an electromagnetic energy exit opening for emission of electromagnetic energy, an air flow ejector adjacent to the electromagnetic energy exit opening including a perimeter wall, the air flow ejector comprising an air duct in flow communication with a distribution system for distributing cooling air, the air flow ejector terminating in a nozzle-like air outlet in the perimeter wall of the light exit opening of the skin treatment applicator, the air duct extending inclined with respect to a direction perpendicular to the light exit opening in the direction of an emission of electromagnetic energy, the method comprising the steps of:

a) exposing a skin target region for a specified duration to irradiation with electromagnetic energy emitted from an electromagnetic energy exit opening of a skin treatment applicator; and b) cooling the skin target region at least during part of the duration of the exposure to the electromagnetic energy irradiation, wherein the step of cooling includes an air cooling step comprising ejection of a directional flow of cooling air towards the skin treatment region, said directional cooling air flow having a temperature T in the interval $0°\text{C.}<T\leq 15°\text{C.}$ 17. The method according to claim 16, wherein the flow is supplied with a temperature between 3 and 15° C.

18. The method according to claim 16, wherein the cooling further comprises at least one contact cooling step provided by a cooled skin contacting surface area of a part of a housing for the skin treatment applicator.

* * * * *